US006215894B1

(12) United States Patent
Zeleny et al.

(10) Patent No.: US 6,215,894 B1
(45) Date of Patent: Apr. 10, 2001

(54) AUTOMATIC IMAGING AND ANALYSIS OF MICROARRAY BIOCHIPS

(75) Inventors: Rolland Zeleny, Sharon; Ron Achin, Marlborough; Mack Schermer, Belmont, all of MA (US)

(73) Assignee: General Scanning, Incorporated, Watertown, MA (US)

( * ) Notice: Subject to any disclaimer, the term of this patent is extended or adjusted under 35 U.S.C. 154(b) by 0 days.

(21) Appl. No.: 09/259,065

(22) Filed: Feb. 26, 1999

(51) Int. Cl.[7] .................................................. G06K 9/00
(52) U.S. Cl. ............................................................ 382/133
(58) Field of Search ..................................... 382/128, 129, 382/133

(56) References Cited

U.S. PATENT DOCUMENTS

| 5,849,486 | * | 12/1998 | Heller et al. | 435/6 |
| 5,874,219 | * | 2/1999 | Rava et al. | 435/6 |
| 5,978,053 | * | 11/1999 | Giles et al. | 349/17 |
| 5,991,030 | * | 11/1999 | Yamamoto et al. | 356/451 |
| 6,139,831 | * | 10/2000 | Shivashankar et al. | 424/82.05 |

\* cited by examiner

Primary Examiner—Andrew W. Johns
Assistant Examiner—Shervin Nakhjavan
(74) Attorney, Agent, or Firm—Cesari & McKenna, LLP

(57) ABSTRACT

A system for scanning biochip arrays includes a unique image array identifier recorded for each array, and a computer-stored record corresponding to each identifier and containing the parameters of the experiment in the array identified by the identifier. The system further includes means for accessing a protocol library to retrieve the scanning protocols associated with the identified arrays and then scanning the arrays in accordance with the respective protocols. The resulting image maps generated by the scanners are stored in locations corresponding to the associated identifiers.

4 Claims, 3 Drawing Sheets

AUTOMATIC IMAGING AND ANALYSIS OF MICROARRAY BIOCHIPS

FIELD OF THE INVENTION

This invention relates to the imaging and analysis of experiments performed on microarry biochips. More particularly it relates to the automatic control of microarry scanners and selection of the proper protocols for analysis of the image maps provided by the scanners.

BACKGROUND OF THE INVENTION

Micrroarray biochips are being increasingly used for the performance of large numbers of closely related chemical tests. For example, to ascertain the genetic differences between lung tumors and normal lung tissue one might deposit small samples of different cDNA sequences under a microscope slide and chemically bond them to the glass. ten thousand or more such samples can easily be arrayed as dots on a single microscope slide using mechanical microarraying techniques. Next, sample mRNA is extracted from normal lung tissue and from a lung tumor. The mRNA represents all of the genes expressed in these tissues and the differences in the expression of mRNA between the diseased tissue and the normal tissue can provide insights into the cause of the cancer and perhaps point to possible therapeutic agents as well. The "probe"samples from the two tissues are labeled with different fluorescent dyes. A predetermined amount of each of the two samples is then deposited on each of the microarray dots where they competitively react with the cDNA molecules. The mRNA molecules that correspond to the cDNA strands in the array dots bind to the strands and those that do not are washed away.

The slide is subsequently processed in a scanner that illuminates each of the dots with laser beams whose wavelengths correspond to the fluorescences of the labeling dyes, The fluorescent emissions are sensed and their intensity measured to ascertain for each of the array dots the degree to which the mRNA samples correspond to the respective cDNA sequences. In the experiment outlined above the image scanner separately senses the two fluorescences and thereby provides separate maps of the reactions of the mRNA extracted from the normal and tumorous tissues. The scanner generates an image map of the array, one for each of the fluorescenses. The maps are ultimately analyzed to provide meaningful information to the experimenter.

Microarray biochips are available in a variety of form factors and they may contain one or more different fluorescence labels. The reagents involved in the chemical reactions in the array dots are typically biological samples such as DNA, RNA, peptides, proteins or other organic molecules. The biochips might be used for diagnostics, screening assays, genetics and molecular biology research. They may include, in addition to the test dots, carlibration dots containing known amounts of the fluorescent materials. Scanning of the latter dots thus serves to calibrate the readings obtained from the test dots.

In order to obtain accurate information from the scanning of a biochip array, it is important to know which fluorescence materials have been used, in where the array is located, and the locations of the calibration dots, if any. It is important to know the fluorescent materials in order to use the correct wavelengths in illuminating the dots and to filter the correct wavelengths of the fluorescent omissions. Furthermore, it is advantageous to excite the fluorescenses with a high intensity so as to provide the maximum signal to the fluorescence detector. However, the intensity must be kept below the level at which the flurorescense is saturated or the fluorescent material is degraded and this depends on the particular fluorescent material that is used.

Furthermore, analysis of raw data collected by the scanner must be performed in accordance with protocols that may vary in accordance with experiment parameters. Prior to the present invention entry of the scanning and analysis protocol has been performed manually. This involves significant operator time and, further, is a source of errors in the scanning and analysis procedure.

SUMMARY OF THE INVENTION

In accordance with the invention an identifier corresponding to each experiment is imprinted on the biochip. The identifier is machine readable and, preferably, also human readable. For example, the identifier may be a number with numerals imprinted on the slide along with a bar code representation of the number. The experiment identifier is imprinted on the chip prior to the deposition of the array experiment. A file folder (i.e., "directory") is opened in a computer system and is logically linked to the array identifier. An operator may enter into that folder the various parameters of the experiment array, e.g., a map of the reagents deposited in the array, identification of the fluorescent tags and the reagents to which they are bonded, and also the locations of any calibration dots on the chip. The operator may also enter into the folder an identification of the scanning and processing protocols to be used in connection with the scanning process. Preferably, however, the system is programmed to retrieve the information from the biochip. The protocols are therefore identified, or even described, in the machine-readable code on the biochip.

Accordingly, when the biochip is subsequently installed in a scanner, the scanner can scan the bar code version of the identifier. The system can then automatically open the requisite file folders and obtain the scanning and analysis protocols. The scanner is then set up to operate in accordance with the retrieved protocol. The resulting image map of the scanned data is stored in one or more files in the chip's file folder. The analysis protocol is subsequently retrieved and the image map processed in accordance with the latter protocol provide an array of output data.

If the system cannot locate an appropriate protocol, either for scanning or processing, it prompts the operator to identify an appropriate stored protocol or to enter a new protocol, if required.

With the foregoing arrangement the requirement for operator intervention is significantly reduced. This speeds up the overall process and, perhaps more important, reduces the probability of error that would be encountered error due to improper entry of scanning and processing protocols.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
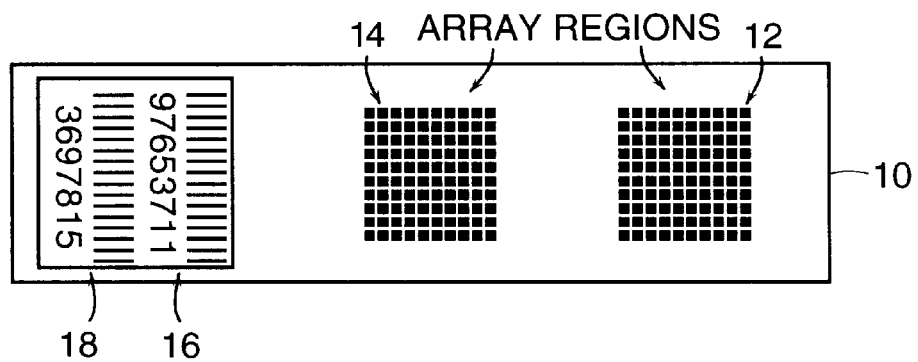
FIG. 1 depicts a biochip containing two experiment

In FIG. 1, a microarray biochip 10 is embodied in the form of a microscope slide than having two array regions 12 and 14. Each of the array regions involves an experiment comprising an array of tests each of which involves a different combination of reagents. The tests are performed by depositing in drops of reagents in locations depicted as dots. The regions 12 and 14 comprise different experiments, in which case the tests in region 12 will be different from those in region 14.

The biochip 10 has also been imprinted with experiment identifiers 16 and 18 relating to the experiments performed in the regions 12 and 14. Specifically, each of the identifiers comprises a numeral (16a,18a) and a corresponding bar code (16b,17b) representation of the numeral, as illustrated in the drawing. The identifier may be a number in which some of the digits identify experiment parameters of the array, others identify the source of the arrays, others may identify the scanning and analysis protocols or even-provide the operating parameters for those protocols, and still others identify the array itself.

Figure 2:
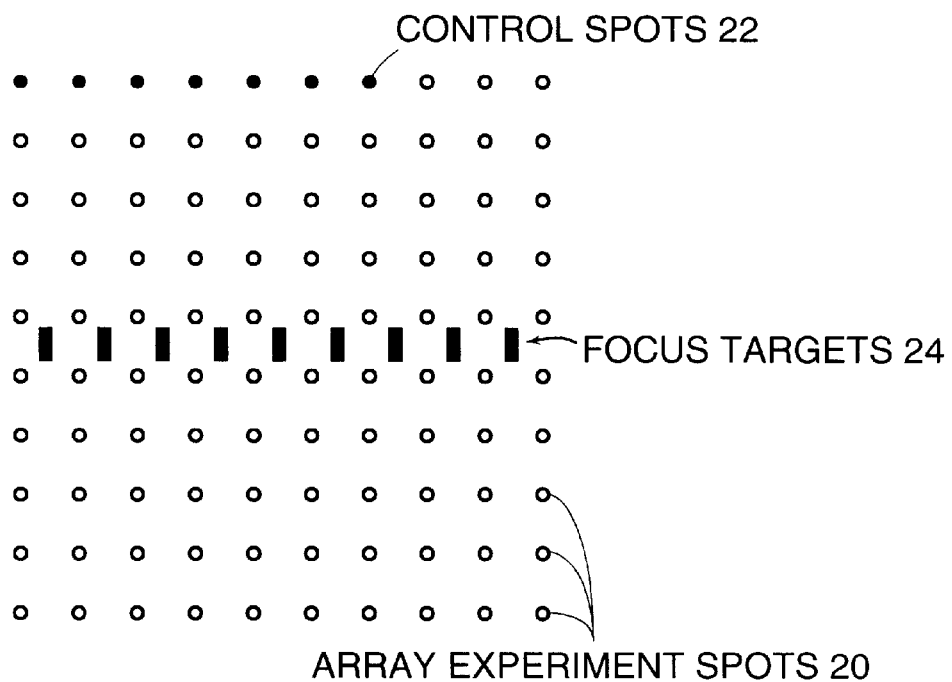
FIG. 2 is an enlargement of a portion of FIG. 1.

A typical array region is depicted in greater detail in FIG. 2. The region comprises an array of test spots 20, and optionally, a series of control spots 22 and focus targets 24. The control spots 22 and the targets 24 are used at the beginning of the scanning process to calibrate and/or adjust the scanner.

Figure 3:
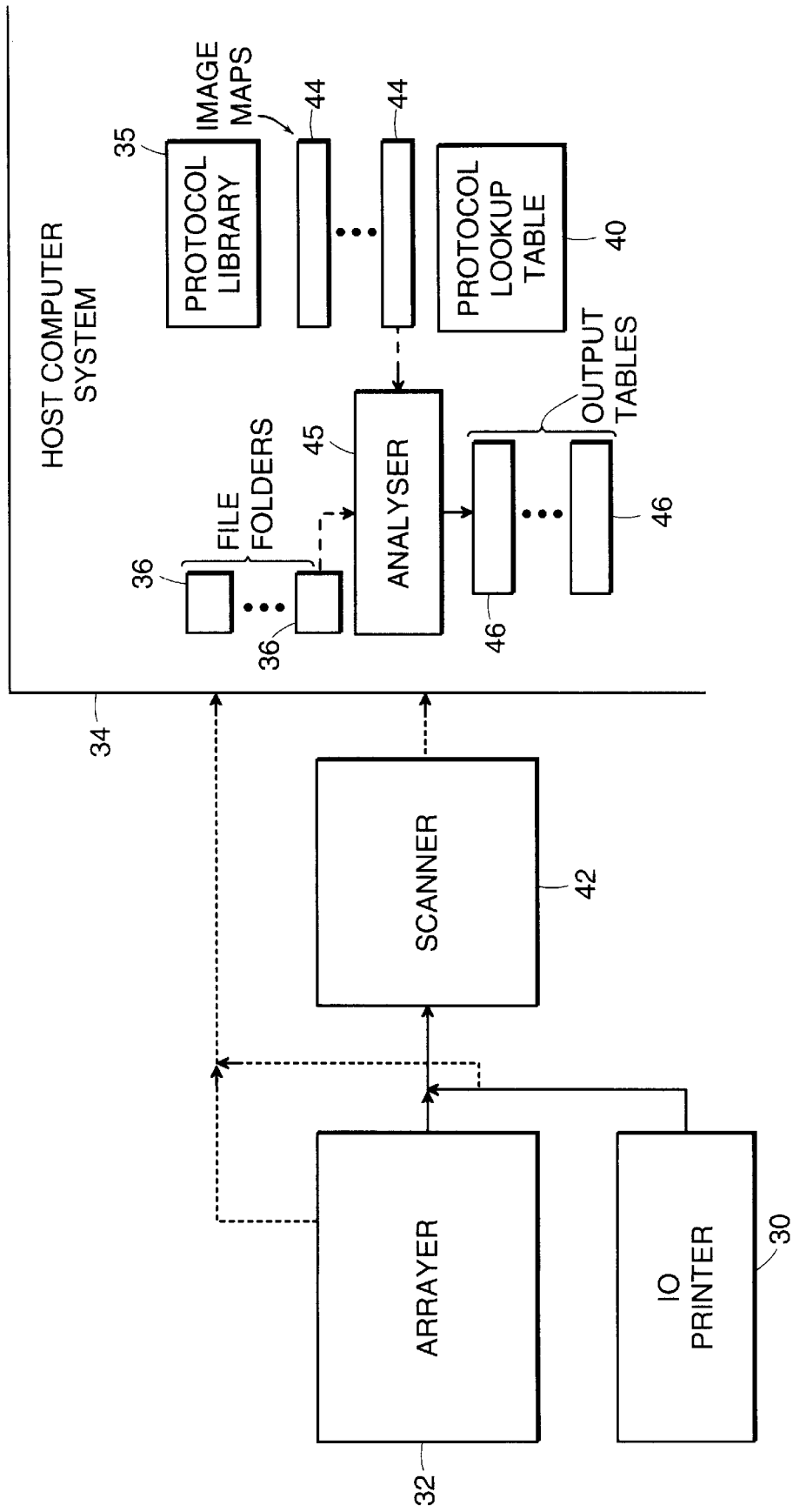
FIG. 3 is a diagram of a system operating in accordance with the invention.

As shown in FIG. 3, a system embodying the invention, includes an identifier printer 30 that imprints the experiment identifiers on the microchips. The chips are loaded into an arrayer 32, where the test spots are deposited to form the experiment arrays.

The biochip subsequently passes to a scanner 42 which first scans the bar codes 16b and 18b. The system 34 responds by opening file folders 36 that are logically linked to the identifiers. In the folders 36 it opens files containing the information in the identifiers. If the bar codes identify protocols contained in a protocol library 35, or if the protocols are contained in the identifier, the system copies the protocols into files in the bio-chip's corresponding file folders. The system then sets up the scanner to operate in accordance with the retrieved scanning protocols.

The image maps obtained by the scanner are stored in image maps 44contained in the folders 36. Finally, an analyzer 45 in the host computer system analyzes the contents of the image maps 44 to provide output tables 46 also stored in the folder 36. In generating an output table the analyzer 45 uses the analysis protocols contained in folders 36.

Figure 4:
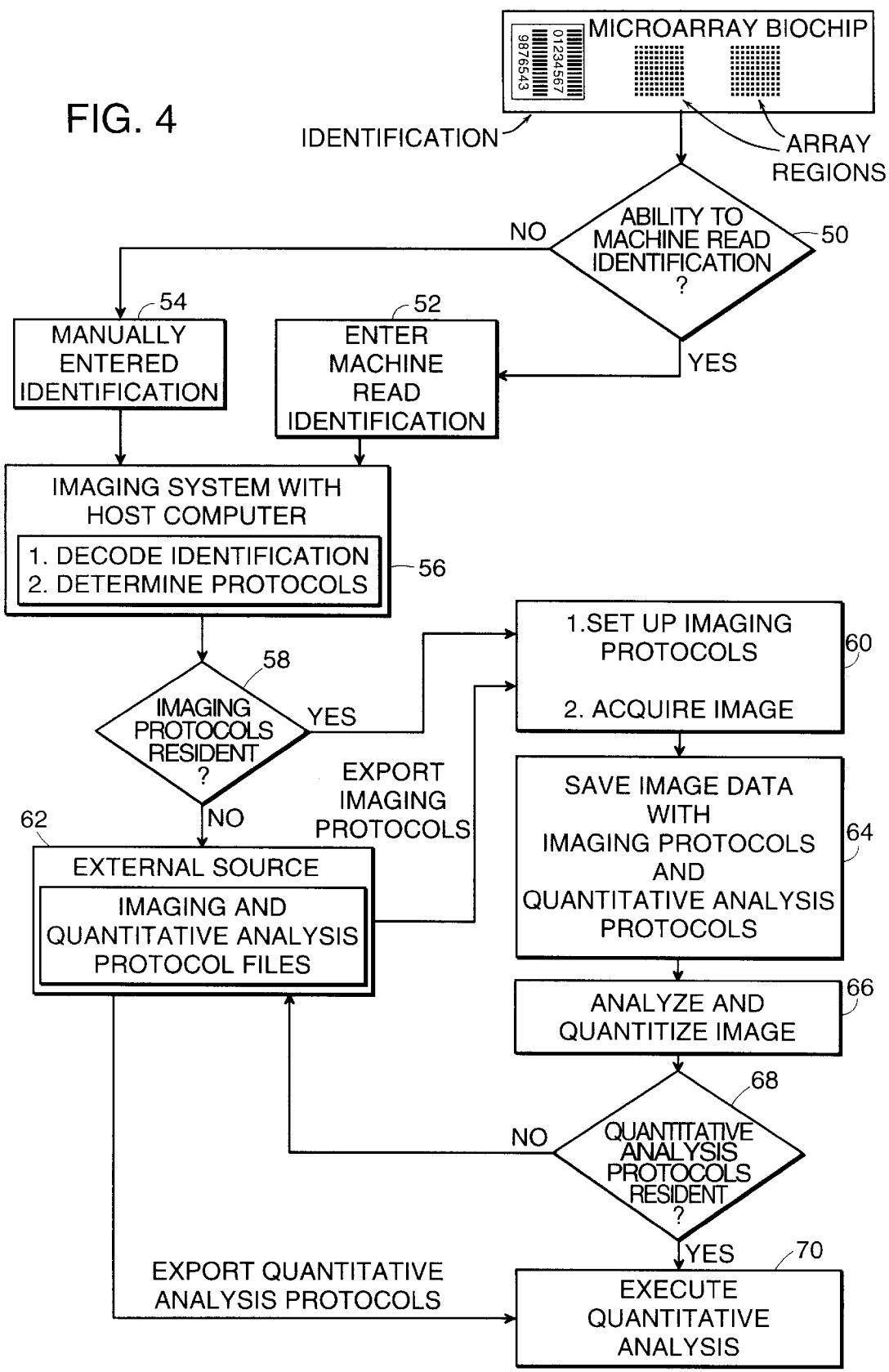
FIG. 4 is a flow diagram of the process of the invention.

A flow diagram of the scanning and image analysis operations is depicted in FIG. 4. When a biochip 10 is loaded into the scanner 42, the scanner, in step 50, attempts to read the array identifiers on the chip. If it can read the identifiers, it transmits them to the host computer system 34 as shown at step 52. If the scanner cannot read the identifiers, it prompts the operator to enter them manually as indicated in step 54. At step 56 the host computer decodes the identifiers and ascertains the protocols that are to be used Assuming the identifier points to protocols, the computer system, at step 58 ascertains whether the protocol library 38 contains a protocol identified in step 56. If it does, the protocol is applied to the scanner 42, which, at step 60, sets up the imaging protocols and acquires the microarray image map. If the library 38 does not contain the identified protocol, it proceeds to step 62 to obtain the protocols from an external source (not shown). The retrieved imaging protocol is then passed to the scanner 42, which operates as indicated in step 60. In step 64, the image maps are recorded in an image file 44.

At a subsequent time, the analysis program is invoked at step 66 and at step 68 the system determines whether the appropriate analysis protocol is resident in the protocol library 38. If it is, the system executes the quantitative analysis at step 70. If the library 38 does not contain the appropriate protocol, the external source is examined, and, it passes the protocol to step 70.

It will be apparent that the foregoing system operates with minimal operator intervention and, therefore, it processes the biochips materially faster than prior arrangements. Moreover, by tying each biochip array to the appropriate protocols at an early stage of the process, it reduces the errors that would otherwise be encountered during the imaging and analysis stages of the procedure. It should be understood that the invention is applicable to biochips other than the biochip illustrated herein. For example, it may be used with "wet" biochips, which contain reagents in liquid form in arrayed wells. Further, as used herein the term "biochip" also applies to materials that are not deposited in ordered arrays, e.g., tissues affixed to slides, which are scanned for fluorescent or other labels.

What is claimed is:

1. A system for processing biochip arrays each of which comprises an experiment consisting of a matrix of tests performed on a biochip, the system compromising A. A plurality of biochips, each biochip carrying an machine-readable array identifier, one or more identifier uniquely identifying an array on the bio chip, B. Means of recording in a computer file corresponding to each identifier, the paramaters of the experiment in the array identified by the identifier, C. A library stored in the computer and containing protocols for imaging the tests in various experiments, D. A bioarray imager, including means for retreiving from biochip the identifiers recorded thereon, E. Means responsive to the retreived identifiers for selecting from the library scanning protocols for the identified arrays, F. Means for controlling the operation of the imager in accordance with the retreived imaging protocols, and G. Means for recording in said computer in a location corresponding to each identifier, and image map generated by said imager in scanning the corresponding experiment array.

2. The system defined in claim 1, including an analysis for anaylizing the recorded image maps, said anaylizer including means for selecting from the library the analysis protocols corresponding to the array identifiers corresponding to the image map.

3. A method of processing biochip arrays, each array comprising one or more experiments, each of which consists of matrix of tests deposited on the biochip, said method comprising the steps of:

A. imprinting on each biochip a machine-readable identifier corresponding to each of said arrays, B. recording in a computer system a file containing, for each identifier, the parameters of the experiments in the arrays identified by the arrray identifiers on the biochip.

C. entering into a library in said computer system, the protocols for for scanning the biochip rays for various experiments, D. in response to each array identifier, selecting from said library the imaging protocols for the experiment in the array identified by the identifier, and E. controlling a scanner in accordance with the selected scanning protocol to scan the identified array and record in said computer system. A corresponding image map of the array.

4. The method defined in claim 3, including the steps of

A; selecting from the protocol library a protocol for the analysis of each of said image maps, and B. Analyzing the image map in accordance with each selected protocol analyzing the image map.

* * * * *